(12) United States Patent
Shiraishi et al.

(10) Patent No.: US 11,980,500 B2
(45) Date of Patent: May 14, 2024

(54) ULTRASOUND DIAGNOSTIC APPARATUS (71) Applicant: Konica Minolta, Inc., Tokyo (JP)

(72) Inventors: Takahiko Shiraishi, Kunitachi (JP); Tatsushi Chihara, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 18/152,982

(22) Filed: Jan. 11, 2023

(65) Prior Publication Data

US 2023/0233185 A1 Jul. 27, 2023

(30) Foreign Application Priority Data

Jan. 24, 2022 (JP) ................................. 2022-008624

(51) Int. Cl.
| | |
|---|---|
| *G06F 3/14* | (2006.01) |
| *A61B 8/00* | (2006.01) |
| *G06F 3/041* | (2006.01) |
| *G06F 3/0481* | (2022.01) |
| *G06F 3/04886* | (2022.01) |
| *H04M 1/02* | (2006.01) |
| *H04M 1/23* | (2006.01) |

(52) U.S. Cl.
CPC ............. *A61B 8/462* (2013.01); *A61B 8/467* (2013.01); *G06F 3/14* (2013.01); *G06F 3/0416* (2013.01); *G06F 3/0481* (2013.01); *G06F 3/04886* (2013.01); *G06F 2203/014* (2013.01); *G06F 2203/04105* (2013.01); *H04M 1/0281* (2013.01); *H04M 1/23* (2013.01); *H04M 2250/22* (2013.01)

(58) Field of Classification Search
CPC ........... A61B 8/462; A61B 8/467; A61B 8/00; A61B 8/4405; A61B 8/4427; A61B 8/461; A61B 8/465; A61B 8/469; A61B 8/54; G06F 3/14; G06F 3/0481; G06F 3/0416; G06F 3/04886; G06F 2203/04105; G06F 2203/014; G06F 3/147; H04M 1/0281; H04M 1/23; H04M 2250/22

See application file for complete search history.

(56) References Cited

U.S. PATENT DOCUMENTS

| | | | | |
|---|---|---|---|---|
| 5,706,553 | A  * | 1/1998 | Riley | ..................... A62B 3/005 |
| | | | | 16/DIG. 18 |
| D395,896 | S  * | 7/1998 | Rosen | .......................... D14/239 |
| 6,669,639 | B1 * | 12/2003 | Miller | ...................... A61B 8/00 |
| | | | | 600/443 |
| 9,454,187 | B2 * | 9/2016 | Aurongzeb | ............... G06F 3/02 |
| 9,946,841 | B2 * | 4/2018 | Jun | ........................ A61B 8/462 |
| 10,064,603 | B2 * | 9/2018 | Lee | ........................... A61B 8/54 |
| 2009/0198132 | A1* | 8/2009 | Pelissier | .................. A61B 8/00 |
| | | | | 600/443 |
| 2011/0169749 | A1* | 7/2011 | Ganey | .................. G06F 1/1626 |
| | | | | 345/173 |

(Continued)

FOREIGN PATENT DOCUMENTS

| | | | | |
|---|---|---|---|---|
| GB | | 2316466 A * | 2/1998 | ............... G06F 1/16 |
| JP | 2017-000421 A | | 1/2017 | |

*Primary Examiner* — Mihir K Rayan
(74) *Attorney, Agent, or Firm* — LUCAS & MERCANTI, LLP (57) ABSTRACT

Provided is an ultrasound diagnostic apparatus including a touch panel monitor and a palm rest that supports a hand when a touch operation is performed on the touch panel monitor.

15 Claims, 8 Drawing Sheets

(56) References Cited

U.S. PATENT DOCUMENTS

| | | | |
|---|---|---|---|
| 2012/0105335 A1* | 5/2012 | Suddreth | G06F 3/0393 345/173 |
| 2013/0237288 A1* | 9/2013 | Lee | G06F 3/0482 455/566 |
| 2013/0300668 A1* | 11/2013 | Churikov | G06F 3/04883 345/173 |
| 2013/0307801 A1* | 11/2013 | Nam | H04M 1/72448 345/173 |
| 2014/0121524 A1* | 5/2014 | Chiang | A61B 8/0891 600/459 |
| 2021/0015456 A1* | 1/2021 | Chiang | A61B 8/0883 |

* cited by examiner

ULTRASOUND DIAGNOSTIC APPARATUS

TECHNICAL FIELD

The present invention relates to an ultrasound diagnostic apparatus.

DESCRIPTION OF THE RELATED ART

In recent years, monitors for ultrasound diagnostic apparatuses have become larger, and display panels with touch panels have become mainstream such that they can be operated more intuitively (see, for example, JP 2017-421 A).

SUMMARY OF THE INVENTION

However, in the ultrasound diagnostic system disclosed in JP 2017-421 A, the touch panel monitor is basically in a vertical posture. Therefore, when a touch operation is performed on the touch panel monitor, it is necessary to place a hand on a screen and to move the hand to up, down, left, and right sides, which causes a problem of hand fatigue. In particular, during ultrasound diagnosis, the above problem becomes significant since a probe is held in one hand.

The present invention has been made in view of the above-described problems, and an object of the present invention is to reduce hand fatigue when a touch operation is performed on a touch panel monitor of an ultrasound diagnostic apparatus.

According to an aspect of the present invention, an ultrasound diagnostic apparatus reflecting one aspect of the present invention includes: a touch panel monitor; and a palm rest that supports a hand when a touch operation is performed on the touch panel monitor.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION

Hereinafter, one or more embodiments of the present invention will be described with reference to the drawings. However, the technical scope of the invention is not limited to the following embodiment and illustrated examples.

<Configuration of Ultrasound Diagnostic Apparatus>

Figure 1:
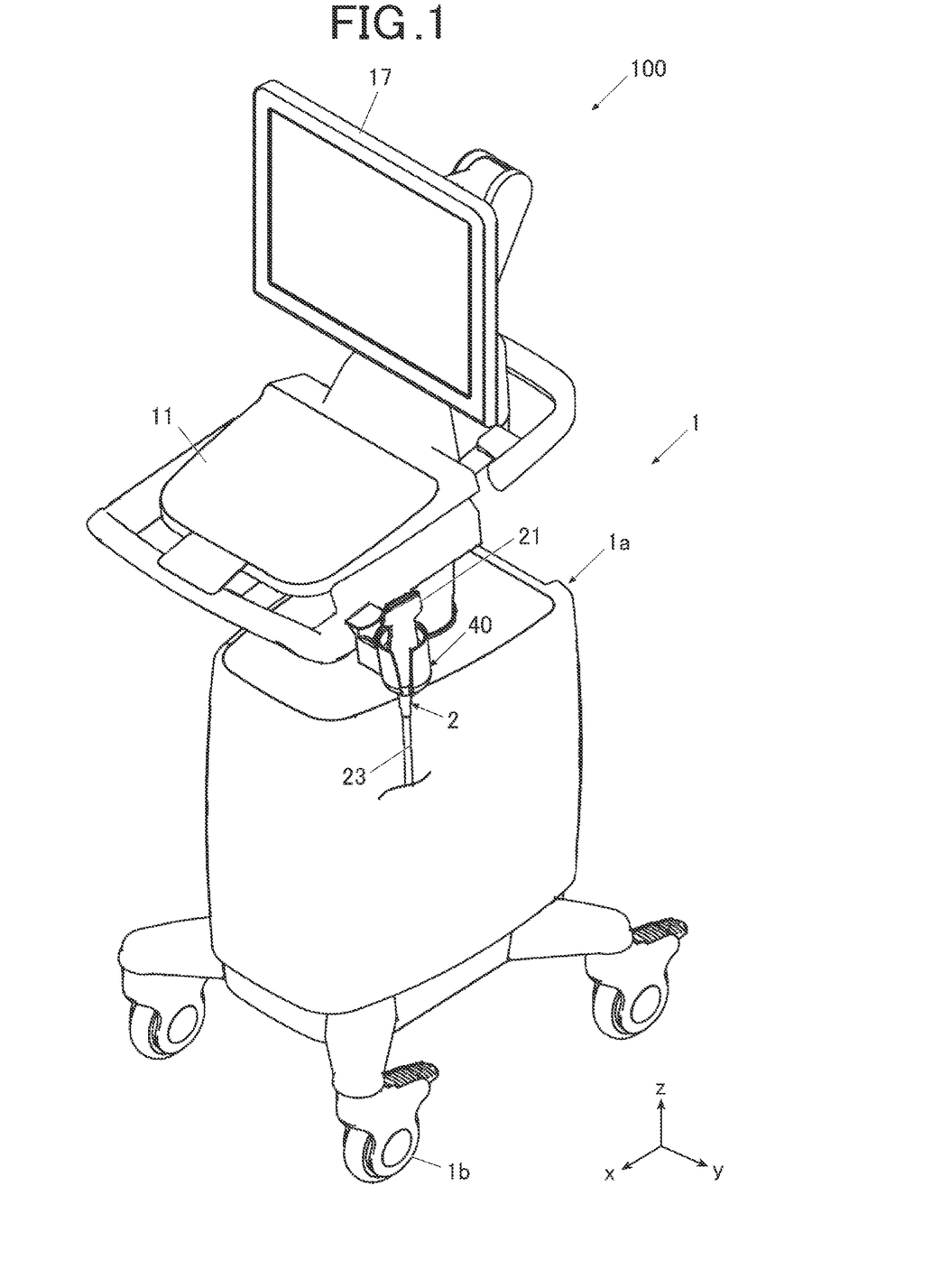
FIG. 1 is a perspective view showing an external configuration of an ultrasound diagnostic apparatus according to an embodiment.
Figure 2:
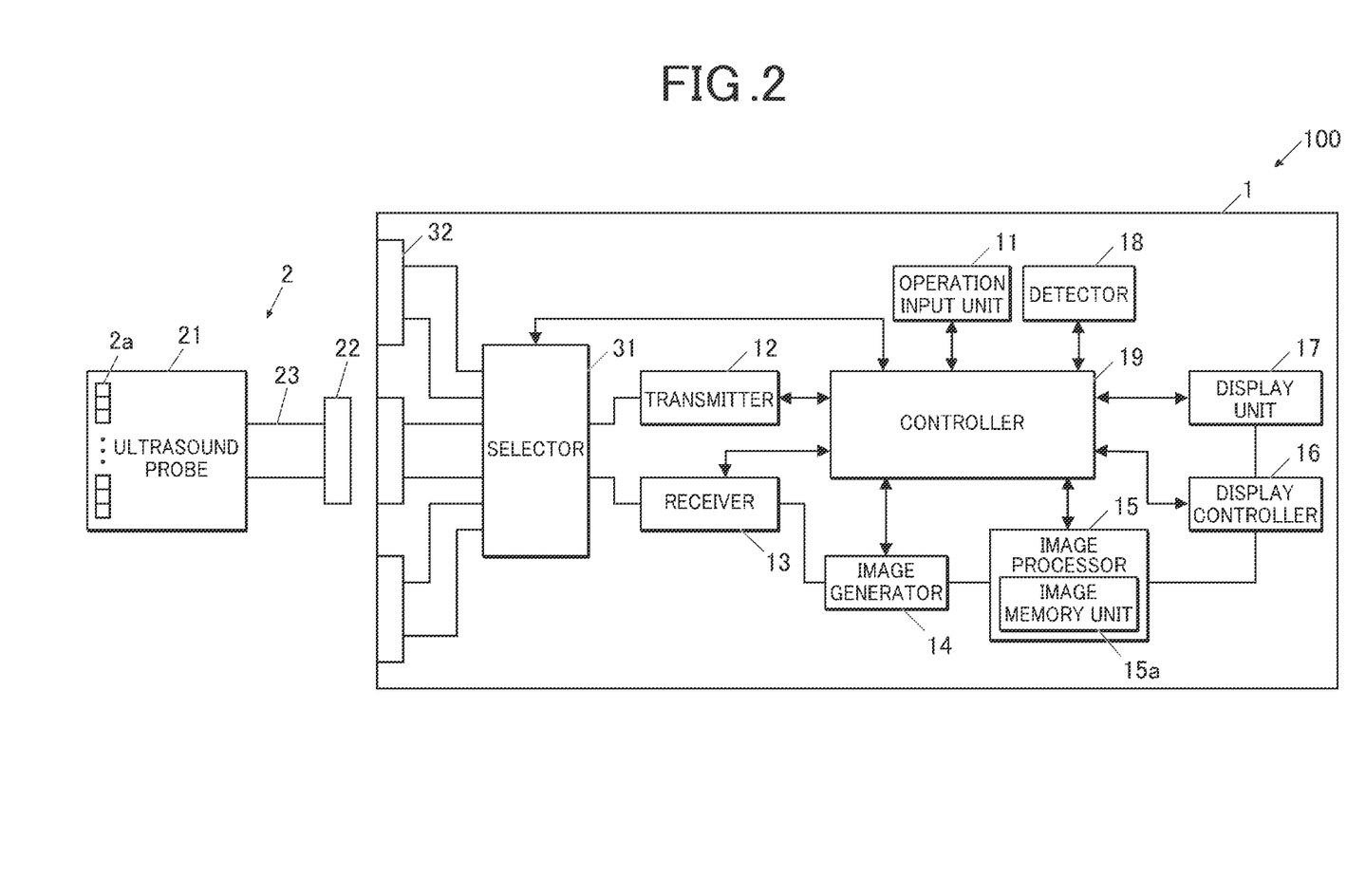
FIG. 2 is a block diagram showing a functional configuration of the ultrasound diagnostic apparatus.

First, the overall configuration of an ultrasound diagnostic apparatus 100 according to this embodiment will be described with reference to FIGS. 1 and 2. FIG. 1 is a perspective view showing the external configuration of the ultrasound diagnostic apparatus 100 according to this embodiment. FIG. 2 is a block diagram showing a functional configuration of the ultrasound diagnostic apparatus 100.

The ultrasound diagnostic apparatus 100 is a movable integrated ultrasound diagnostic apparatus that is installed in, for example, a medical examination room of a medical facility such as a hospital. As shown in FIGS. 1 and 2, the ultrasound diagnostic apparatus 100 includes an ultrasound diagnostic apparatus main body 1 and an ultrasound probe 2. The ultrasound probe 2 transmits ultrasonic waves (transmission ultrasonic waves) to the inside of a subject, such as a living body of a patient, and receives reflected waves (reflected ultrasonic waves: echoes) of the ultrasonic waves reflected in the subject. The ultrasound diagnostic apparatus main body 1 is connected to the ultrasound probe 2, transmits a driving signal, which is an electric signal, to the ultrasound probe 2 to direct the ultrasound probe 2 to transmit ultrasonic waves to the subject, and images the internal state of the subject as ultrasound image data on the basis of a received signal, which is an electric signal generated by the ultrasound probe 2 according to the reflected ultrasonic waves from the inside of the subject received by the ultrasound probe 2.

Here, an x-axis, a y-axis, and a z-axis are taken as shown in FIG. 1. The ultrasound diagnostic apparatus main body 1 has an operation inputter 11, a display 17, connectors 32 (FIG. 2 (not shown in FIG. 1)), an ultrasound probe holder 40, and casters 1b on a housing 1a. Here, as an example, a configuration in which three connectors 32 are provided on a side surface of the housing 1a will be described. However, the number of connectors is not limited to three. Correspondingly to this, a configuration in which three ultrasound probe holders 40 are provided on a side surface of the housing 1a will be described (however, two ultrasound probe holders are not shown in FIG. 1). However, the number of ultrasound probe holders is not limited to three. The housing 1a is made of metal, resin, or the like and accommodates circuit components and the like which will be described below.

The operation inputter 11 is disposed on a top surface (+z side) of the housing 1a. The operation inputter 11 includes operation elements for receiving the input of various image parameters for displaying a command for a diagnosis start instruction, data, such as personal information of the subject, ultrasound image data, and the like on the display 17 and receives operation inputs to the operation elements from a user, such as a doctor or a technician. It is assumed that the operation elements are, for example, a push button, an encoder (rotary knob), a lever switch, a joystick, a trackball, a keyboard, a touch sensor (not shown) that is provided on the display 17, and multifunction switches which are combinations of them.

The display (touch panel monitor) 17 is vertically provided on the top surface (+z side) of the housing 1a. The display 17 has a display panel, such as a liquid crystal display (LCD), an organic electro-luminescence (EL) display, or an inorganic EL display, and various types of display information, such as ultrasound images, are displayed on a display screen of the display panel.

The connector 32 is a receptacle connector that electrically connects (a connector 22 (FIG. 2) of) the ultrasound probe 2. The ultrasound probe holder 40 is a (probe) holder that holds the ultrasound probe 2. The caster 1b is a moving part, such as a wheel, that is disposed on a bottom surface (−z side) of the housing 1a and enables the ultrasound diagnostic apparatus 100 (ultrasound diagnostic apparatus main body 1) to move on a floor surface as an xy plane. The ultrasound diagnostic apparatus 100 can be moved to a position, such as the right side or the left side of the patient as the subject, by the casters 1b.

The ultrasound probe 2 has an ultrasound probe main body 21, the connector 22, and an ultrasound probe cable 23. The ultrasound probe main body 21 includes, for example, transducers 2a and an acoustic lens (not shown) that concentrates the transmission ultrasonic waves on a focus. For example, a plurality of (for example, 192) transducers 2a are arranged in a one-dimensional array in an azimuth direction. In addition, the transducers 2a may be arranged in a two-dimensional array. Further, the number of transducers 2a can be set to any value. Furthermore, a linear-scanning-type electronic scanning probe is adopted as the ultrasound probe 2 and is illustrated. However, either an electronic scanning type or a mechanical scanning method may be adopted. In addition, any of the linear scanning type, a sector scanning type, and a convex scanning type can be adopted. Further, the three ultrasound probes 2 of different scanning types described above can be connected to the connectors 32 of the ultrasound diagnostic apparatus main body 1 at the same time.

The ultrasound probe main body 21 transmits ultrasonic waves from the transducers 2a to the subject in response to the driving signal input from the ultrasound diagnostic apparatus main body 1, receives the reflected ultrasonic waves from the subject with the transducers 2a, generates a received signal, and outputs the received signal to the ultrasound diagnostic apparatus main body 1.

The connector 22 is a plug connector that is fitted and electrically connected to the connector 32. The ultrasound probe cable 23 is a signal line that is electrically connected between the ultrasound probe main body 21 and the connector 22 and is configured by covering a plurality of insulated wires with a (protective) coating layer.

Next, a functional configuration of the ultrasound diagnostic apparatus 100 will be described with reference to FIG. 2. As shown in FIG. 2, the ultrasound diagnostic apparatus main body 1 includes the operation inputter 11, a transmitter 12, a receiver 13, an image generator 14, an image processor 15, a display controller 16, a display 17, a detector 18, a controller 19, a selector 31, and the connector 32 inside or outside the housing 1a.

The operation inputter 11 receives an operation input from an operator through various operation elements and outputs operation information of the operation input to the controller 19.

The transmitter 12 is a circuit that supplies a driving signal, which is an electric signal, to the ultrasound probe 2 through the selector 31 and the connector 32 to direct the ultrasound probe 2 to generate transmission ultrasonic waves, under the control of the controller 19. In addition, the transmitter 12 includes, for example, a clock generation circuit, a delay circuit, and a pulse generation circuit. The clock generation circuit is a circuit that generates a clock signal for determining the transmission timing and transmission frequency of the driving signal. The delay circuit is a circuit that sets a delay time for each individual path corresponding to each transducer 2a and delays the transmission of the driving signal by the set delay time to focus transmission beams composed of the transmission ultrasonic waves. The pulse generation circuit is a circuit that generates a pulse signal as the driving signal with a predetermined period. The transmitter 12 having the above-described configuration drives, for example, some successive transducers 2a (for example, 64 successive transducers) among the plurality of (for example, 192) transducers 2a which are arranged in the ultrasound probe 2 to generate the transmission ultrasonic waves. Then, the transmitter 12 performs scanning by shifting the transducer 2a to be driven in the azimuth direction (scanning direction) whenever the transmission ultrasonic waves are generated.

The receiver 13 is a circuit that receives a received signal, which is an electric signal, from the ultrasound probe 2 through the connector 32 and the selector 31 under the control of the controller 19. The receiver 13 includes, for example, an amplifier, an A/D conversion circuit, and a phasing addition circuit. The amplifier is a circuit that amplifies the received signal with a preset amplification factor for each individual path corresponding to each transducer 2a. The A/D conversion circuit is a circuit that performs analog-to-digital conversion (A/D conversion) for the amplified received signal. The phasing addition circuit is a circuit that gives a delay time to each individual path corresponding to each transducer 2a to adjust a time phase and adds (performs phasing addition for) the individual paths to generate sound ray data, for the received signal subjected to the A/D conversion.

Under the control of the controller 19, the image generator 14 can generate brightness (B)-mode image data that consists of pixels having brightness values as received energy by performing, for example, an envelope detection process or logarithmic compression on the sound ray data from the receiver 13 and adjusting a dynamic range and gain to convert brightness. That is, the B-mode image data represents the strength of the received signal by brightness. The image generator 14 may be capable of generating ultrasound image data in other image modes, such as an amplitude (A) mode, a motion (M) mode, and an image mode based on a Doppler method (for example, a color Doppler mode), in addition to the B-mode image data as ultrasound image data whose image mode is the B-mode.

The image processor 15 performs image processing on the B-mode image data output from the image generator 14 according to various image parameters, which are being set, under the control of the controller 19. In addition, the image processor 15 includes an image memory 15a that is configured by a semiconductor memory such as a dynamic random access memory (DRAM). The image processor 15 stores the B-mode image data subjected to the image processing in units of frames in the image memory 15a under the control of the controller 19. In some cases, image data in units of frames is referred to as ultrasound image data or frame image data. The image processor 15 sequentially outputs the image data generated as described above to the display controller 16 under the control of the controller 19.

Under the control of the controller 19, the display controller 16 converts the image data received from the image processor 15 into an image signal for display and outputs the image signal for display to the display 17.

The detector 18 has a touch sensor (not shown) that is provided in a palm rest 171, which will be described below, and detects that the operator's hand is placed on the palm rest 171. When the detector 18 detects that the operator's hand is placed on the palm rest 171, it outputs detection information to the controller 19.

The controller 19 includes, for example, a central processing unit (CPU), a read only memory (ROM), and a random access memory (RAM), reads various processing programs, such as system programs, stored in the ROM, develops the programs in the RAM, and controls the operation of each unit of the ultrasound diagnostic apparatus 100 according to the developed programs. The ROM is configured by a nonvolatile memory, such as a semiconductor, and stores, for example, a system program corresponding to the ultrasound diagnostic apparatus 100, various processing programs executable on the system program, and various types of data such as gamma tables. These programs are stored in the form of computer-readable program codes, and the CPU sequentially performs operations corresponding to the program codes. The RAM forms a work area that temporarily stores various programs executed by the CPU and data related to these programs.

The selector 31 is a circuit that switches the connector 32 as an ultrasonic wave transmission and reception target (to which the transmitter 12 outputs a driving signal and from which the receiver 13 receives a received signal) under the control of the controller 19.

Some or all of the functions of each functional block of each unit included in the ultrasound diagnostic apparatus 100 can be implemented as hardware circuits such as integrated circuits. The integrated circuit is, for example, a large scale integration (LSI), and the LSI is also called an integrated circuit (IC), a system LSI, a super LSI, and an ultra LSI, depending on a difference in the degree of integration. In addition, a circuit integration method is not limited to the LSI and may be implemented by a dedicated circuit or a general-purpose processor.

Further, a field programmable gate array (FPGA) or a reconfigurable processor in which the connections and settings of circuit cells in an LSI are reconfigurable may be used. In addition, some or all of the functions of each functional block may be implemented by software. In this case, this software is stored in one or more storage media, such as ROMs, optical discs, and hard disks. This software is executed by an arithmetic processor.

Next, the palm rest 171 provided on the display 17 will be described with reference to FIGS. 3A and 3B.

Figure 3A:
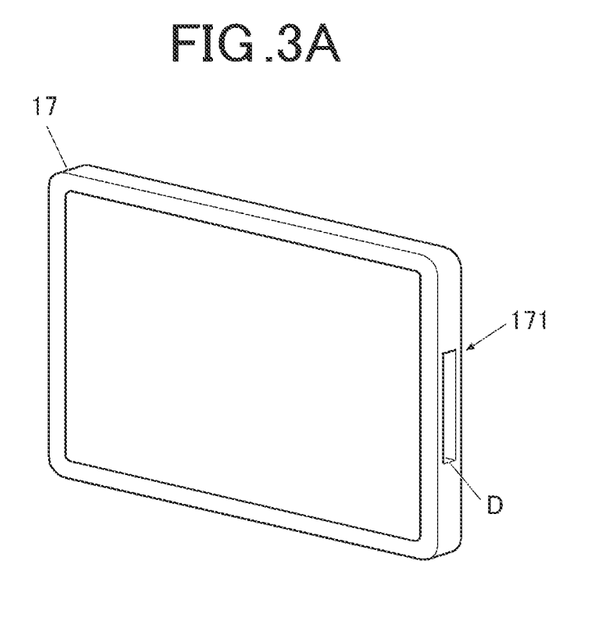
FIG. 3A is a perspective view showing an example of a palm rest.
Figure 3B:
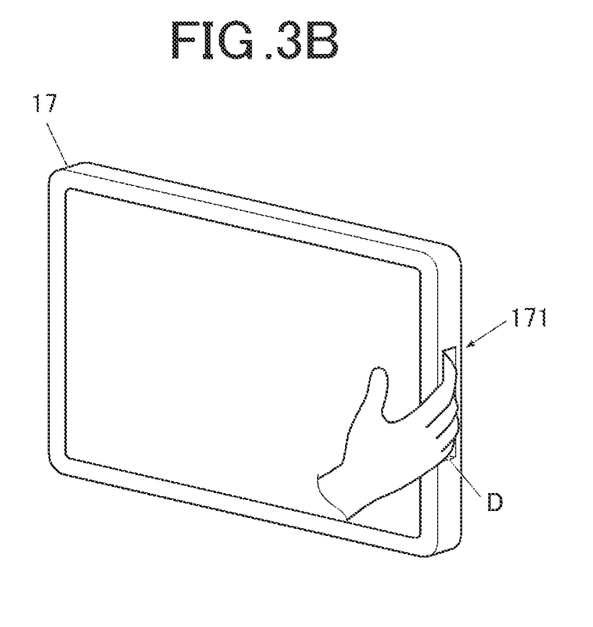
FIG. 3B is a diagram showing a state in which an operator's hand is placed on the palm rest.

FIG. 3A is a perspective view showing an example of the palm rest 171, and FIG. 3B is a diagram showing a state in which the operator's hand is placed on the palm rest 171. In addition, FIGS. 3A and 3B show only the display 17 of the ultrasound diagnostic apparatus 100 (this holds for FIGS. 4A to 6B).

As shown in FIGS. 3A and 3B, the palm rest 171 is configured by a vertically elongated groove D that is provided in a right side surface of a housing of the display 17. This groove D is of such a size that four fingers (an index finger, a middle finger, a ring finger, and a little finger) of the right hand excluding the thumb can be inserted at the same time. Therefore, when performing a touch operation on the display 17, the operator can insert the four fingers into the palm rest 171 and support the palm rest 171 with the right hand. As a result, it is possible to reduce hand fatigue during the touch operation. The position where the palm rest 171 is provided is not limited to the right side surface of the housing of the display 17, and the palm rest 171 may be provided in a left side surface of the housing or both side surfaces (the left side surface and the right side surface) of the housing.

Figure 4A:
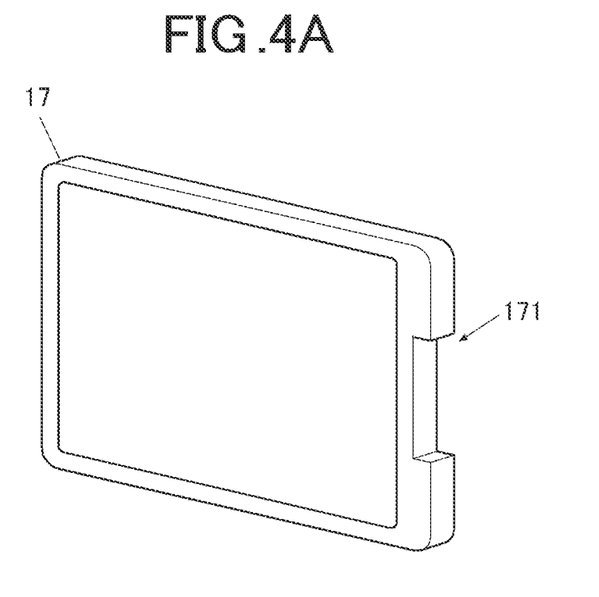
FIG. 4A is a perspective view showing an example of the palm rest.
Figure 4B:
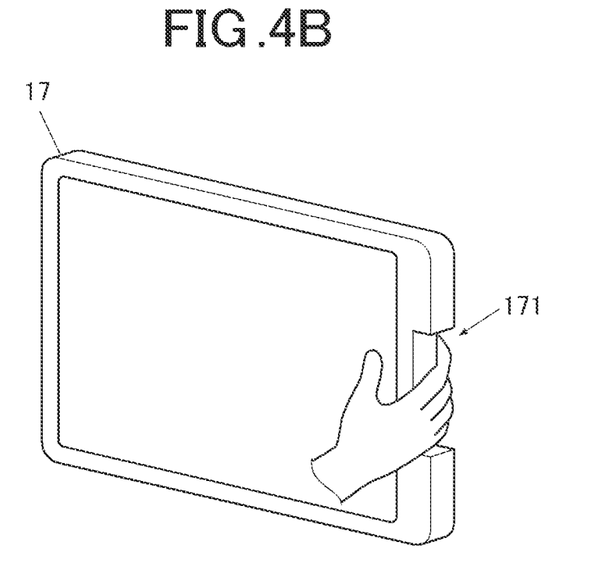
FIG. 4B is a diagram showing a state in which the operator's hand is placed on the palm rest.

The palm rest 171 may be configured by providing a notch in the right side surface of the housing of the display 17 as shown in FIGS. 4A and 4B. For example, this notch has a sufficient size to accommodate four fingers of the right hand excluding the thumb at the same time. Therefore, when performing a touch operation on the display 17, the operator can place the four fingers on the palm rest 171 and support the palm rest 171 with the right hand. As a result, it is possible to reduce hand fatigue during the touch operation.

Figure 5A:
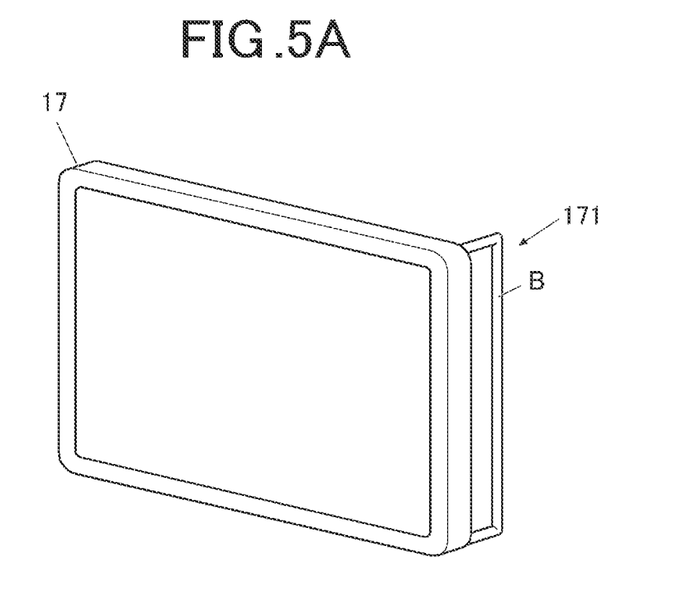
FIG. 5A is a perspective view showing an example of the palm rest.
Figure 5B:
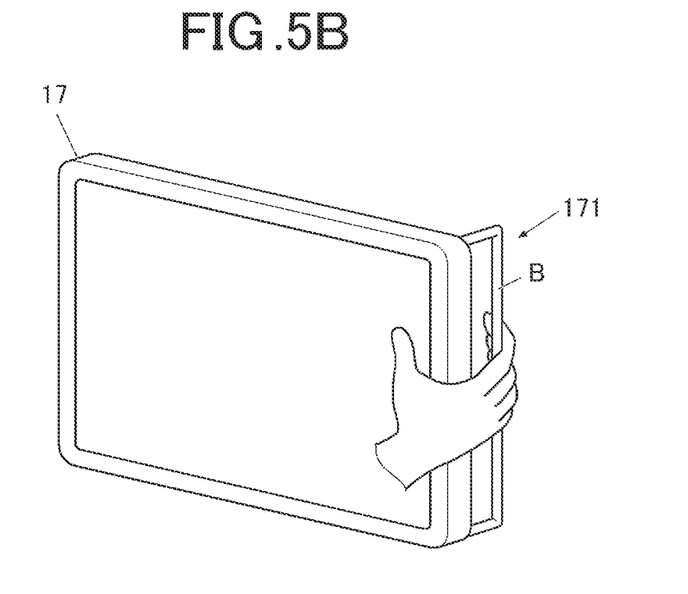
FIG. 5B is a diagram showing a state in which the operator's hand is placed on the palm rest.
Figure 6A:
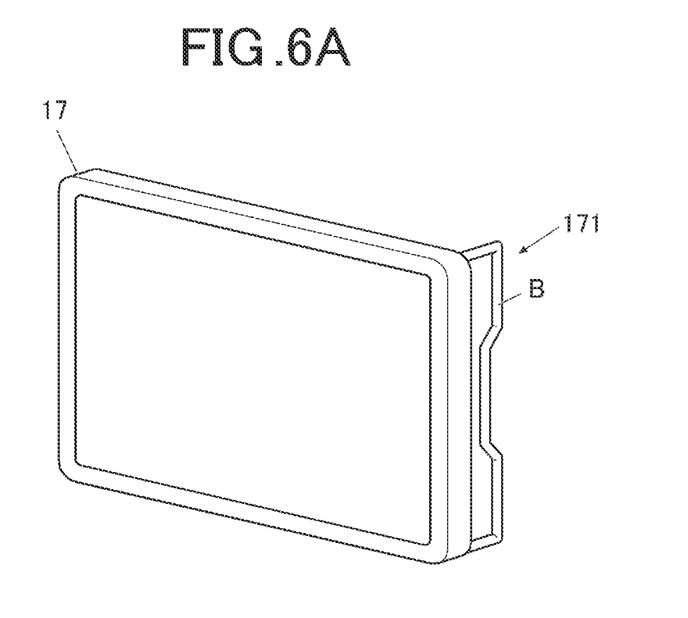
FIG. 6A is a perspective view showing an example of the palm rest.
Figure 6B:
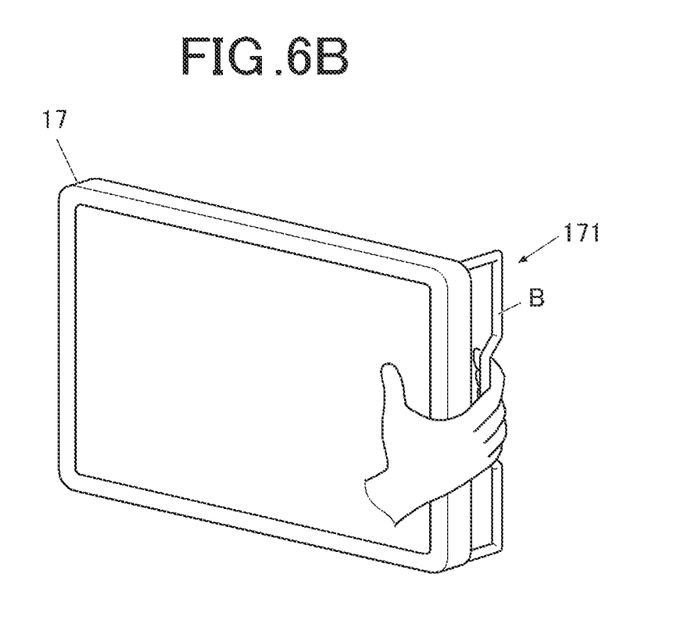
FIG. 6B is a diagram showing a state in which the operator's hand is placed on the palm rest.

Further, as shown in FIGS. 5A and 5B, the palm rest 171 may be configured by vertically providing a bar B, which extends from one end to the other end of the display 17 in the vertical direction (z-axis direction; see FIG. 1), that is, a bar B which is formed in a substantially U-shape, in the −x direction (see FIG. 1) on the rear surface of the right side of the housing of the display 17. In this case, the palm rest 171 also functions as a buffer member that reduces an external impact on the display 17. For example, the bar B is of such a size that the operator can hold the bar B with four fingers of the right hand excluding the thumb at the same time, with the ball of the right hand (the base of the thumb) attached to the right front surface of the housing of the display 17. In addition, the bar B is not limited to the case in which it has a linear shape from one end to the other end. For example, as shown in FIGS. 6A and 6B, a middle portion of a bar from one end to the other end may be bent to provide a recess (dent) for facilitating the support of four fingers of the right hand excluding the thumb. The position where each of the palm rests 171 shown in FIGS. 5A, 5B, 6A, and 6B is provided is not limited to the right side surface of the housing of the display 17, and each palm rest 171 may be provided on the left side surface of the housing or both side surfaces (the left side surface and the right side surface) of the housing, similarly to each of the palm rests 171 shown in FIGS. 3A, 3B, 4A, and 4B.

Figure 7:
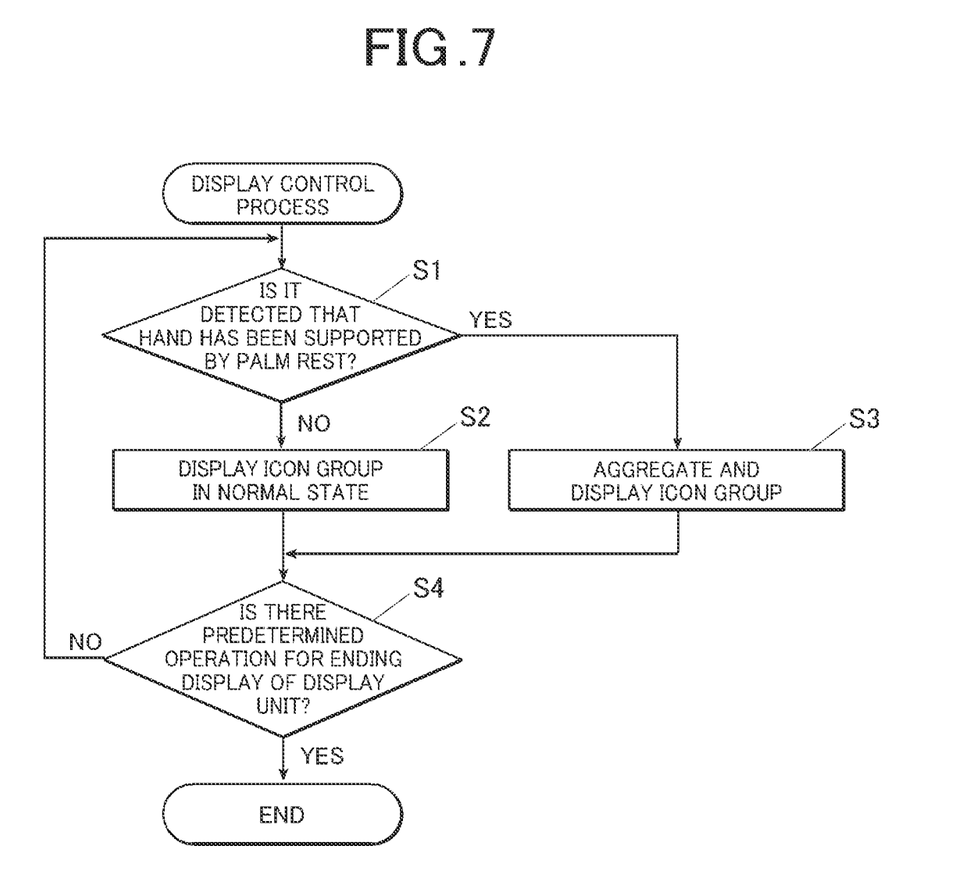
FIG. 7 is a flowchart showing a control procedure of a display control process.

Next, a display control process for an icon group G that is displayed on the display 17 so as to be touched and operated will be described with reference to FIG. 7. FIG. 7 is a flowchart showing a control procedure of the display control process.

As shown in FIG. 7, when the display control process is started, first, the controller 19 determines whether or not the detector 18 has detected the support of the hand by the palm rest 171 (Step S1).

Figure 8A:
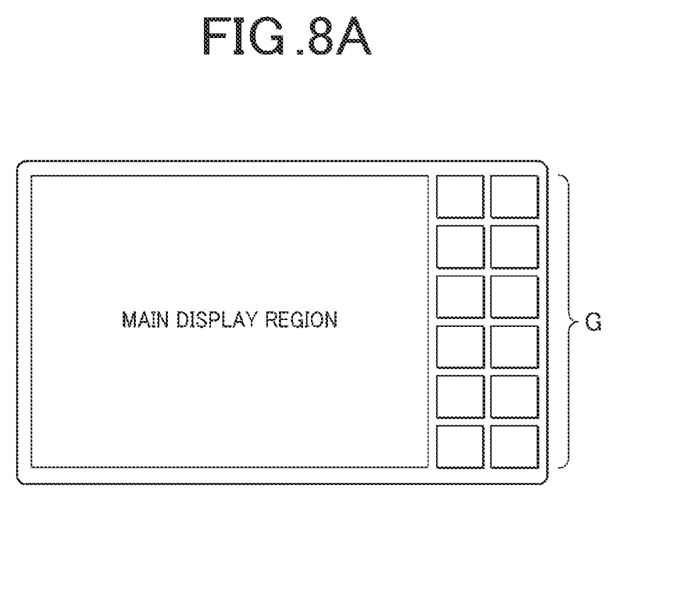
FIG. 8A is a diagram showing an example of a display screen when an icon group is displayed on a display in a normal state.

When it is determined in Step S1 that the detector 18 has not detected the support of the hand by the palm rest 171 (Step S1; NO), the controller 19 directs the display controller 16 to display the icon group G on the display 17 in a normal state (ordinary state) as shown in FIG. 8A (Step S2). Here, in the normal state, for example, 12 icons of the icon group G are displayed in six rows and two columns from the top to the bottom of an icon display region on the right side of a main display region in which ultrasound image data and the like are displayed.

Figure 8B:
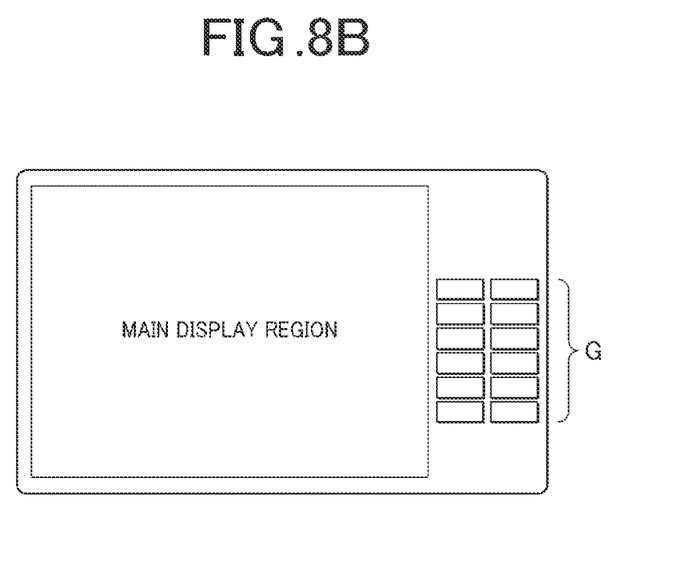
FIG. 8B is a diagram showing an example of the display screen when an icon group in an aggregated state is displayed on the display.

Further, when it is determined in Step S1 that the detector 18 has detected the support of the hand by the palm rest 171 (Step S1; YES), the controller 19 directs the display controller 16 to display the icon group G in an aggregated state on the display 17 as shown in FIG. 8B. Here, in the aggregated state, 12 icons of the icon group G are displayed in six rows and two columns in the center of the icon display region. In other words, in the aggregated state, each icon of the icon group G is reduced and displayed at a position (range) that the thumb (see FIG. 3B) of the right hand of the operator supported by the palm rest 171 can reach, that is, at a position that can be touched and operated by the thumb.

Then, the controller 19 determines whether or not a predetermined operation (for example, an operation for an end button (not shown)) for ending the display of the display 17 has been performed (Step S4).

When it is determined in Step S4 that the predetermined operation for ending the display of the display 17 has not been performed (Step S4; NO), the controller 19 returns the process to the determination process in Step S1 and repeatedly performs the subsequent processes.

In addition, when it is determined in Step S4 that the predetermined operation for ending the display on the display 17 has been performed (Step S4; YES), the controller 19 ends the display control process.

As described above, the ultrasound diagnostic apparatus 100 includes the display (touch panel monitor) 17 and the palm rest 171 that supports the hand when a touch operation on the display 17 is performed.

Therefore, according to the ultrasound diagnostic apparatus 100, the palm rest 171 can support the hand when a touch operation is performed on the display 17. Therefore, it is possible to reduce hand fatigue when a touch operation is performed on the display 17 of the ultrasound diagnostic apparatus 100.

In addition, according to the ultrasound diagnostic apparatus 100, since the palm rest 171 supports the hand that touches and operates the display 17, the operator's body is less likely to shake. As a result, it is possible to easily stabilize the hand that holds the ultrasound probe 2 and is opposite to the hand touching and operating the display 17. Therefore, it is possible to smoothly capture an ultrasound image.

Further, the ultrasound diagnostic apparatus 100 includes the controller 19 that controls the display of the display 17. When the icon group (objects) G that can be touched and operated is displayed on the display 17, the controller 19 can display the icon group G in a display mode in which a touch operation can be performed in a state in which the hand is supported by the palm rest 171.

Therefore, according to the ultrasound diagnostic apparatus 100, it is possible to perform the touch operation on the icon group G while maintaining the state in which the hand is supported by the palm rest 171. As a result, it is possible to further reduce hand fatigue when a touch operation is performed on the display 17 of the ultrasound diagnostic apparatus 100.

In addition, when the icon group (a plurality of objects) G is displayed in a display aspect in which a touch operation can be performed in a state in which the hand is supported by the palm rest 171, the controller 19 of the ultrasound diagnostic apparatus 100 displays the icon group G in the aggregated state. Therefore, even when the number of icons constituting the icon group G is large, it is possible to suitably touch and operate each icon.

Further, the ultrasound diagnostic apparatus 100 includes the detector 18 that detects that the hand has been supported by the palm rest 171. When the detector 18 detects that the hand has been supported by the palm rest 171, the controller 19 displays the icon group G in the display mode in which a touch operation can be performed in a state in which the hand is supported by the palm rest 171.

Therefore, according to the ultrasound diagnostic apparatus 100, when the hand has been supported by the palm rest 171, it is possible to automatically switch the display mode of the icon group G to a display mode in which a touch operation can be performed in a state in which the hand is supported by the palm rest 171. Therefore, it is possible to improve the operability of the icon group G.

Furthermore, when the detector 18 does not detect that the hand has been supported by the palm rest 171, the controller 19 of the ultrasound diagnostic apparatus 100 displays the icon group G in the normal state (ordinary state).

Therefore, according to the ultrasound diagnostic apparatus 100, when the hand is not supported by the palm rest 171, it is possible to automatically switch the display mode of the icon group G to a normal display mode. As a result, it is possible to improve the operability of the icon group G.

The present invention has been specifically described above on the basis of the embodiment. However, the present invention is not limited to the above-described embodiment and can be modified without departing from the gist of the present invention.

For example, in the display control process according to the above-described embodiment, the icon group G that is displayed on the display 17 so as to be touched and operated is the object to be subjected to display control. However, the object to be subjected to display control may be any object that can be touched and operated and includes, for example, a toolbar, a button, and a slider.

Further, in the above-described embodiment, the palm rest on which the operator's hand can be placed may be provided at the lower end of the display 17 on the front side of the display 17. In this case, the detector 18 detects that the operator's hand is placed on the palm rest. Then, when the detector 18 detects that the operator's hand has been placed on the palm rest, the controller 19 displays the icon group G in a display mode in which the icon group G can be touched and operated in a state in which the hand is placed on the palm rest. Specifically, the controller 19 aggregates and displays the icon group G in the center of a lower portion of the screen of the display 17.

Furthermore, in the above-described embodiment, when the number of icons constituting the icon group G is greater than a predetermined number (for example, 12), in the display of the icon group G in the aggregated state on the display 17 in the process of Step S3 in the display control process, for example, these icons may be distributed and displayed on a plurality of pages. In this case, for example, both a forward button and a backward button are used to switch to the page on which the icon to be operated is displayed.

In addition, the specific details of the configurations and control described in the above-described embodiment can be appropriately changed without departing from the gist of the present disclosure. Further, the configurations and control described in the above-described embodiment can be appropriately combined without departing from the gist of the present disclosure.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2022-008624, filed on Jan. 24, 2022, including description, claims, drawings and abstract is incorporated herein by reference in its entirety.

The invention claimed is:

1. An ultrasound diagnostic apparatus comprising:
   a touch panel monitor;

a palm rest that supports a hand when a touch operation is performed on the touch panel monitor, the palm rest including a bar having a portion that extends parallel to and is separated from a side of a housing of the touch panel monitor;

a controller that controls display of the touch panel monitor; and a detector that detects a supported state when the hand of the user is supported by the palm rest, wherein when the detector detects the supported state, the controller displays icons in an aggregated state at a position that is reachable a user's hand supported by the palm rest.

2. The ultrasound diagnostic apparatus according to claim 1, wherein the palm rest is provided on at least one of left and right sides of the touch panel monitor.

3. The ultrasound diagnostic apparatus according to claim 2, wherein the portion of the bar extends in a vertical direction and functions as a buffer member that reduces an external impact on the touch panel monitor.

4. The ultrasound diagnostic apparatus according to claim 1, wherein the portion of the bar is configured to be held by four fingers of the user's hand while a ball of the user's hand rests against the side.

5. The ultrasound diagnostic apparatus according to claim 4, wherein the portion of the bar further includes at least one bend providing a recess for facilitating support of the four fingers of the user's hand.

6. The ultrasound diagnostic apparatus according to claim 1, wherein the bar is formed in a U-shape on a rear surface of the side of the housing, with the portion of the bar being a base of the U-shape.

7. The ultrasound diagnostic apparatus according to claim 1, wherein, when the detector does not detect that the hand has been supported by the palm rest, the controller displays the icons in a normal state.

8. An ultrasound diagnostic apparatus comprising:

a touch panel monitor;

a palm rest that supports a hand when a touch operation is performed on the touch panel monitor, the palm rest including a bar having a portion that extends parallel to and is separated from a side of a housing of the touch panel monitor;

a controller that controls display of the touch panel monitor, wherein, when an object that is capable of being touched and operated is displayed on the touch panel monitor, the controller is capable of displaying the object in a display mode in which the touch operation is capable of being performed in a state in which the hand is supported by the palm rest; and a detector that detects that the hand has been supported by the palm rest, wherein, when the detector detects that the hand has been supported by the palm rest, the controller displays the object in the display mode.

9. The ultrasound diagnostic apparatus according to claim 8, wherein, when a plurality of the objects are displayed in the display mode, the controller aggregates and displays the plurality of objects.

10. The ultrasound diagnostic apparatus according to claim 8, wherein, when the detector does not detect that the hand has been supported by the palm rest, the controller displays the object in a normal state.

11. The ultrasound diagnostic apparatus according to claim 8, wherein the palm rest is provided on at least one of left and right sides of the touch panel monitor.

12. The ultrasound diagnostic apparatus according to claim 11, wherein the portion of the bar extends in a vertical direction and functions as a buffer member that reduces an external impact on the touch panel monitor.

13. The ultrasound diagnostic apparatus according to claim 8, wherein the portion of the bar is configured to be held by four fingers of the user's hand while a ball of the user's hand rests against the side.

14. The ultrasound diagnostic apparatus according to claim 13, wherein the portion of the bar further includes at least one bend providing a recess for facilitating support of the four fingers of the user's hand.

15. The ultrasound diagnostic apparatus according to claim 8, wherein the bar is formed in a U-shape on a rear surface of the side of the housing, with the portion of the bar being a base of the U-shape.

* * * * *